(12) United States Patent
Pierpont et al.

(10) Patent No.: US 8,357,138 B2
(45) Date of Patent: Jan. 22, 2013

(54) ANGIOPLASTY METHOD AND MEANS FOR PERFORMING ANGIOPLASTY

(75) Inventors: Brien E. Pierpont, St. Petersburg, FL (US); James A. Coyle, Somerville, MA (US)

(73) Assignee: Pierpont Family Limited Partnership, St. Petersburg, FL (US)

( * ) Notice: Subject to any disclaimer, the term of this patent is extended or adjusted under 35 U.S.C. 154(b) by 1788 days.

(21) Appl. No.: 11/616,372

(22) Filed: Dec. 27, 2006

(65) Prior Publication Data

US 2007/0135792 A1   Jun. 14, 2007

Related U.S. Application Data

(62) Division of application No. 10/773,925, filed on Feb. 6, 2004, now abandoned.

(60) Provisional application No. 60/446,001, filed on Feb. 7, 2003.

(51) Int. Cl.
*A61M 31/00* (2006.01)

(52) U.S. Cl. ............... 604/509; 604/507; 604/96.01; 604/103.03

(58) Field of Classification Search .......... 604/507–509, 604/96.01, 103.03, 103.04
See application file for complete search history.

(56) References Cited

U.S. PATENT DOCUMENTS

| | | |
|---|---|---|
| 3,395,710 A | 8/1968 | Stratton et al. |
| 4,581,017 A | 4/1986 | Sahota |
| 4,744,366 A | 5/1988 | Jang |
| 4,771,777 A | 9/1988 | Horzewski et al. |
| 4,832,028 A | 5/1989 | Patel |
| 4,932,959 A | 6/1990 | Horzewski et al. |
| 4,944,745 A | 7/1990 | Sogard et al. |
| 4,988,356 A * | 1/1991 | Crittenden et al. ........... 606/192 |
| 5,019,042 A | 5/1991 | Sahota |
| 5,035,705 A | 7/1991 | Burns |
| 5,059,178 A | 10/1991 | Ya |
| 5,085,636 A | 2/1992 | Burns |
| 5,102,390 A | 4/1992 | Crittenden et al. |
| 5,158,540 A | 10/1992 | Wijay et al. |
| 5,178,608 A | 1/1993 | Winters |
| 5,180,367 A | 1/1993 | Kontos et al. |
| 5,299,575 A | 4/1994 | Sandridge |
| 5,484,412 A * | 1/1996 | Pierpont ................ 604/101.03 |
| 5,489,271 A | 2/1996 | Andersen |
| 5,554,118 A | 9/1996 | Jang |
| 6,398,799 B2 | 6/2002 | Kramer |
| 2002/0165574 A1 | 11/2002 | Ressemann et al. |
| 2002/0165598 A1 | 11/2002 | Wahr et al. |

FOREIGN PATENT DOCUMENTS

| | | |
|---|---|---|
| EP | 0 415 332 A1 | 3/1991 |
| EP | 0 565 996 A1 | 10/1993 |

* cited by examiner

*Primary Examiner* — Laura Bouchelle
(74) *Attorney, Agent, or Firm* — Zarley Law Firm, P.L.C.

(57) ABSTRACT

An angioplasty catheter assembly having an anchoring catheter within a guide catheter such that the anchoring catheter anchors to the guide catheter and the inner wall of a coronary artery; the anchoring catheter has an opening in its tubular wall such that a guide wire and balloon dilatation catheter can be disposed therethrough and extending through the length of the anchoring catheter.

10 Claims, 5 Drawing Sheets

ANGIOPLASTY METHOD AND MEANS FOR PERFORMING ANGIOPLASTY

CROSS REFERENCE TO RELATED APPLICATIONS

This application is a divisional of application Ser. No. 10/773,925 filed Feb. 6, 2004 now abandoned which is a non-provisional filed from provisional patent application Ser. No. 60/446,001 filed Feb. 7, 2003.

BACKGROUND OF THE INVENTION

Cardiac catheterization and angioplasty are common medical procedures. U.S. Pat. No. 5,484,412 describes an angioplasty procedure wherein a balloon dilatation catheter is movably positioned within an anchoring catheter, which in turn is located within a guiding catheter. Optionally, internal balloons in the anchoring catheter can be inflated to anchor it to the balloon dilatation catheter. External balloons on the anchoring catheter can be inflated to anchor it to the inside of the guiding catheter. The balloons can be selectively inflated and deflated. Other external balloons on the distal outer surface of the anchoring catheter can be inflated to secure the anchoring catheter within the blood vessel beyond the distal end of the guiding catheter. Optional perforations in the wall of the anchoring catheter permit blood to enter and exit, especially while external balloons are inflated.

Using the anchoring catheter during an angioplasty procedure, the conventional guiding catheter is first inserted into the blood vessel to a location proximal to the narrowing targeted for treatment. The conventional guidewire, balloon dilatation catheter, and anchoring catheter are then inserted through the guiding catheter with the anchoring catheter and balloon dilatation catheter optionally being secured together by the internal balloons on the anchoring catheter. When the guidewire, dilatation catheter and anchoring catheter exit the distal end of the guiding catheter, the internal balloons are collapsed, if they were inflated, and the spaced external balloons are inflated to secure the anchoring catheter to both the guiding catheter and the interior of the blood vessel. The balloon dilatation catheter is then extended through the end of the anchoring catheter to perform its conventional function with respect to the narrowed section of the blood vessel.

Despite this advancement in the art, problems still remain. In U.S. Pat. No. 5,484,412, the entry point of the guidewire and balloon dilatation catheter into the anchoring catheter is at the proximal end of the anchoring catheter. Consequently, it is difficult to maintain the position of the guidewire down the coronary artery while loading the anchoring catheter onto the back end of the guidewire. Also, by having the entry point of the guidewire and balloon dilatation catheter at the proximal end of the anchoring catheter, the guidewire must extend through the entire catheter. If the anchoring catheter is loaded on the back of the guidewire, the guidewire would have to be withdrawn or extended in length until the wire extended out the back end of the anchoring catheter to allow the operator to grasp the guidewire while advancing the anchoring catheter. Furthermore, if the anchoring catheter needs to be withdrawn or exchanged, it is difficult to hold the guidewire in place without extending it or exchanging it for an exchange-length guidewire. It is important for the operator to have control of the guidewire during advancement or retraction of the balloon dilatation catheter and/or the anchoring catheter so as not to lose the guidewire position in the vessel being treated.

Known in the art are a variety of means for inserting a guidewire through the side of a balloon dilatation catheter. Examples of such devices are disclosed in U.S. Pat. Nos. 5,489,271 and 5,554,118. While these devices assist in inserting or exchanging a balloon dilatation catheter, they do not incorporate the use of or the advantages associated with the use of an anchoring catheter to maintain the position of the guidewire, the balloon dilatation catheter, and the guiding catheter within the coronary artery.

Thus, a primary object of the present invention is to provide an angioplasty catheter assembly that has an anchoring catheter with an opening in its side wall so that the guidewire and balloon dilatation catheter may extend there through.

Another object of the present invention is to provide an angioplasty catheter assembly that allows for a guidewire to be maintained in its position down the coronary artery.

Yet another object of the present invention is to provide an angioplasty catheter assembly that does not cause the guidewire to have to be withdrawn, extended or exchanged for a longer guidewire to allow the operator to grasp the guidewire while advancing an anchoring catheter.

Another object of the present invention is to provide an angioplasty catheter assembly that helps prevent the loss of the guidewire position within the coronary artery.

Another object of the present invention is to provide an angioplasty catheter assembly having a longitudinal slit along the anchoring catheter to allow an operator to extend the guidewire through the tubular wall of the anchoring catheter at multiple positions.

These and other objects, features, or advantages of the present invention will become apparent from the specification and claims. Although some descriptions of the invention refer to angioplasty systems, dilatation balloons, balloon dilatation catheters and treatment of coronary arteries, it should be understood that such elements are merely exemplary and the invention can be used in conjunction with a variety of treatment catheters and in different vessels of the human body. Treatment catheters can include treatment elements such as, for example, angioplasty balloons, stents and stent delivery components and radiation therapy apparatuses.

SUMMARY OF THE INVENTION

The present invention is for a catheter assembly that uses a hollow guiding catheter having an elongated hollow anchoring catheter disposed within. The anchoring catheter has an external anchoring balloon member that is adapted to inflate to engage the guiding catheter. Optionally, the anchoring catheter has an internal anchoring balloon member that is adapted to inflate to engage and retain a dilatation catheter against movement with respect to the anchoring catheter. The anchoring catheter additionally has an opening in its tubular wall in order to allow the balloon dilatation catheter and/or a guidewire to pass through the opening and extend out the distal end of the anchoring catheter. The opening in the tubular wall of the anchoring catheter can be a longitudinal slit that allows the entry point of the guidewire and balloon dilatation catheter to change.

DESCRIPTION OF THE PREFERRED EMBODIMENT

Figure 1:
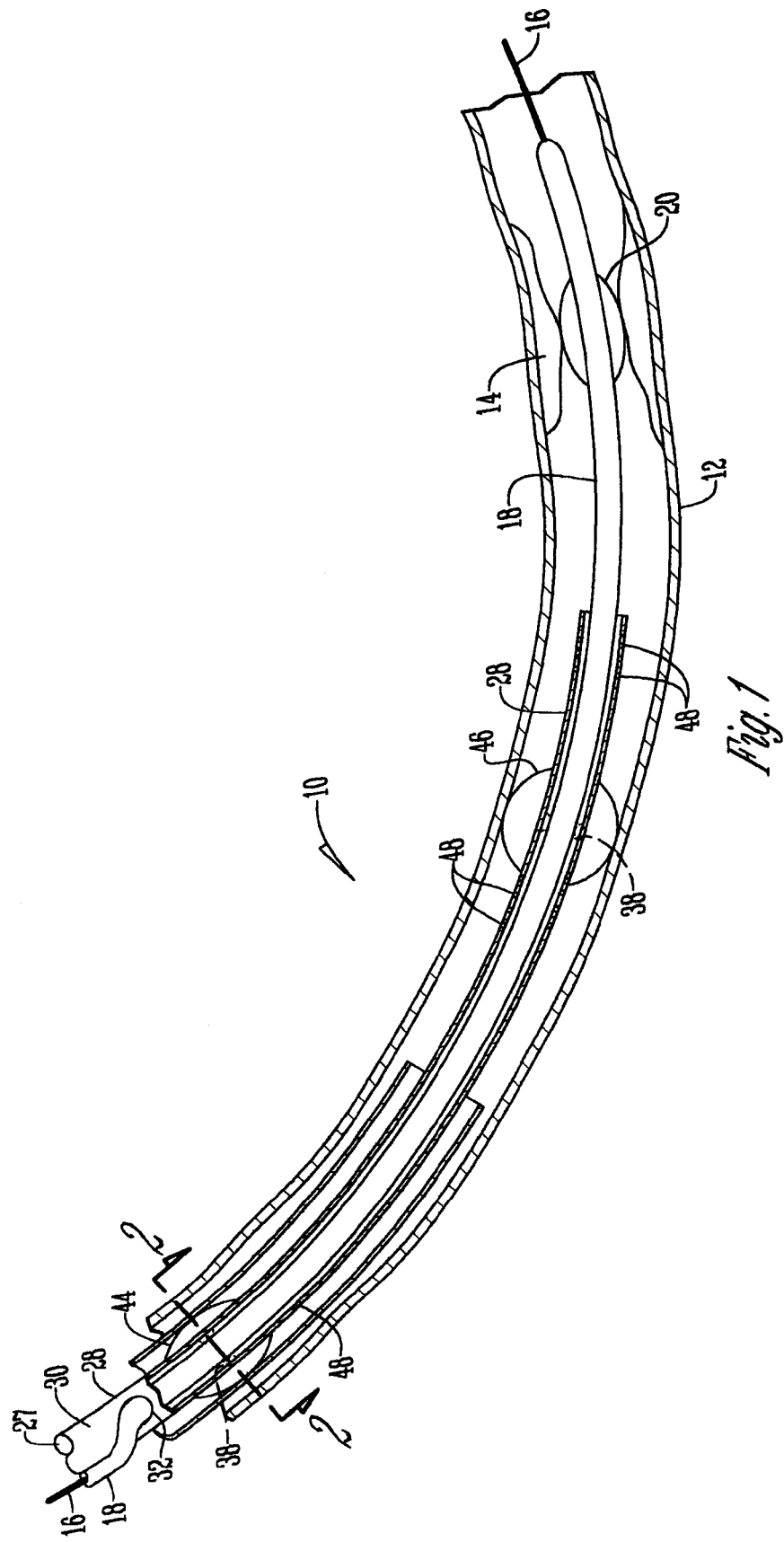
FIG. 1 is a sectional view of an angioplasty catheter assembly in accordance with the invention, shown within a coronary artery.
Figure 2:
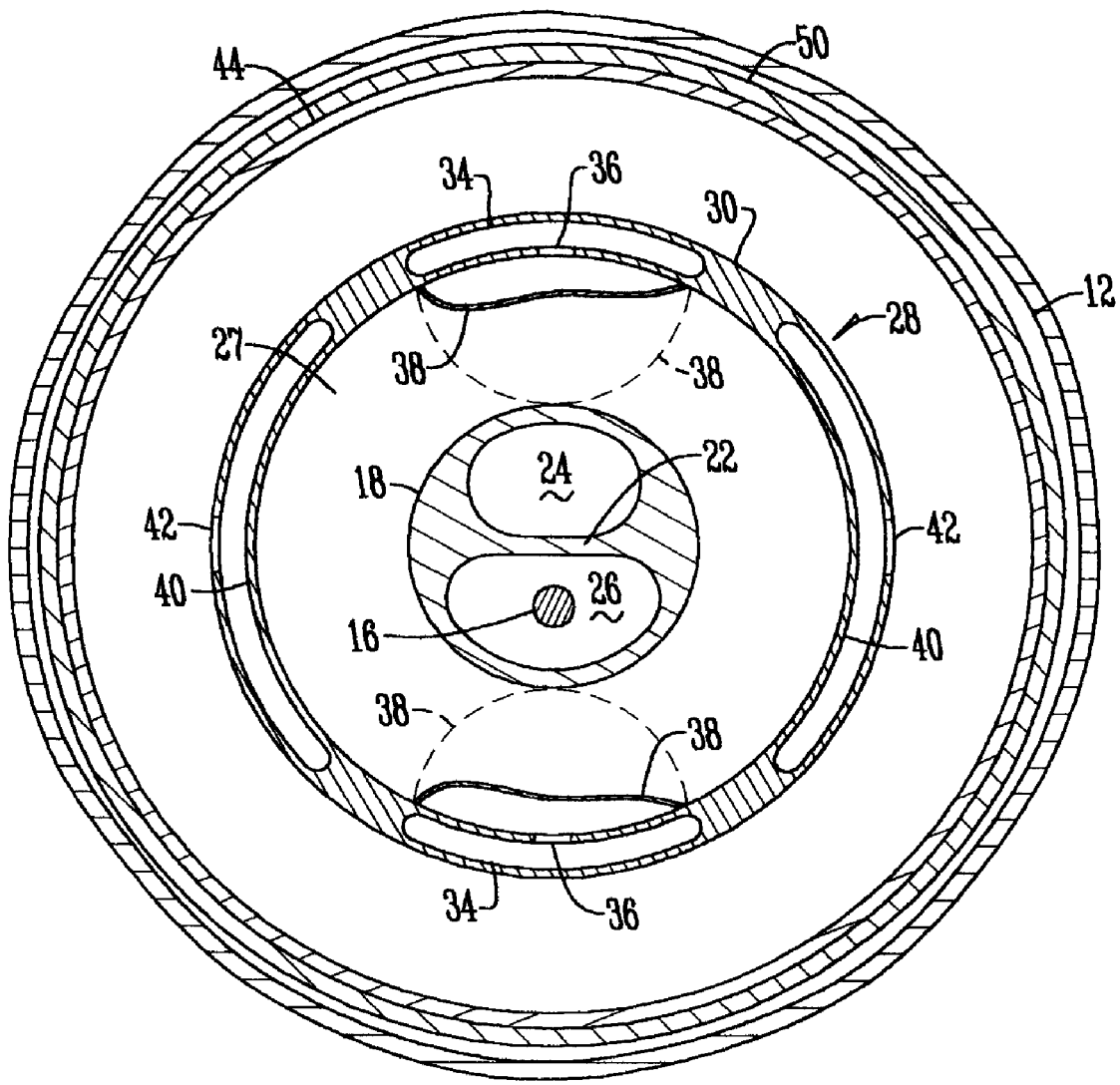
FIG. 2 is an enlarged cross-sectional view taken on line 2-2 of FIG. 1.
Figure 3:
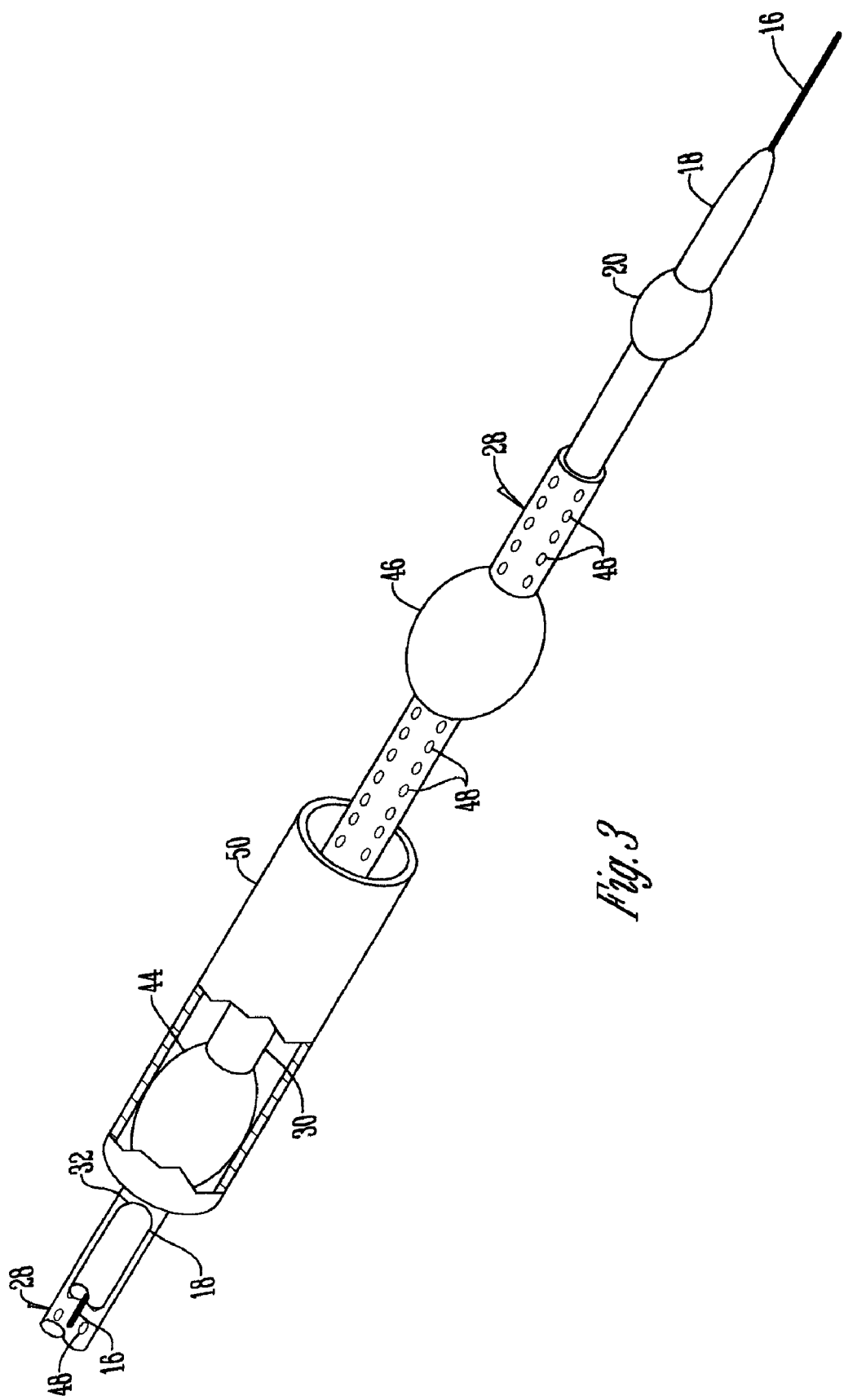
FIG. 3 is a large scale sectional-perspective view of the forward or distal ends of the balloon dilatation, anchoring and guiding catheters in accordance with the invention.

The present invention is an improvement over the catheter assembly disclosed in U.S. Pat. No. 5,484,412 incorporated by reference in its entirety herein. The angioplasty catheter assembly 10 of the present invention is shown in FIG. 1. The catheter assembly 10 is placed within a coronary artery 12 having plaque or obstruction 14. Reference numeral 16 reveals a conventional guidewire over which a treatment or balloon dilatation catheter 18 is slidably mounted. In this example, an over-the-wire balloon dilatation catheter is described, but other treatment catheters may be used such as a rapid exchange dilatation catheters or stent delivery catheters. Dilatation catheter 18 has an inflatable balloon 20 on the distal end thereof and has its internal diameter divided by membrane 22 to create a balloon inflation passageway or lumen 24 and a guidewire passageway or lumen 26 as shown in FIG. 2.

The balloon dilatation catheter 18 and guidewire 16 are slidably mounted within the hollow interior or lumen 27 of an anchoring catheter 28. The anchoring catheter 28 has an outer tubular wall 30 having distal and proximal ends and an opening 32, through which the balloon dilatation catheter 18 and guidewire 16 are slidably mounted. Optionally, the outer wall 30 of the anchoring catheter 28 has at least one and possibly two hollow elongated internal balloon inflation passageways 34, each of which has a port 36. In this optional embodiment, one or more flexible internal anchoring balloons 38 extend inwardly within the hollow interior of the anchoring catheter 28 and extend over ports 36.

The outer wall 30 of anchoring catheter 28 has one or more external balloon passageways 40 each having an external port 42. A first concentric anchoring external balloon 44 extends outwardly from wall 30 over a single port 42, and a second external concentric anchoring balloon 46 also extends over a port 42. Opening 32 may be disposed proximally of, and preferably adjacent to, balloon 44. Optionally, a plurality of blood perfusion ports 48 extend through the wall of anchoring catheter 28 at locations both proximal and distal of balloon 46. The anchoring catheter 28 is adapted to be disposed through guiding catheter 50.

In operation, as an example, the guiding catheter 50 is inserted into the groin of the patient and positioned at the origin of the coronary artery 12. The balloon dilatation catheter 18 is inserted over guidewire 16 and both the guidewire 16 and balloon dilatation catheter 18 are then inserted through opening 32 of anchoring catheter 28. The assembled balloon dilatation catheter 18 and anchoring catheter 28 are moved as a unit through guiding catheter 50. At this point in time, the external balloons 44 and 46 of anchoring catheter 28 are still deflated.

The above-described assembled components are extended through the guiding catheter 50 until the guidewire 16 and the distal end of the anchoring catheter 28 extend distally beyond the distal end of the guiding catheter 50. At that point in time, the external balloons 44 and 46 are inflated. The external balloon 46 engages the inner wall of coronary artery 12 while the external balloon 44 engages the interior of guiding catheter 50. This secures the guiding catheter 50 to the coronary artery 12. The balloon dilatation catheter 18 is now moveable independent of the anchoring catheter 28 and is thereupon moved to a position where the dilatation balloon 20 is adjacent to plaque or obstruction 14.

When inflated within coronary artery 12, external balloon 46 also temporarily occludes or blocks blood flow through coronary artery 12, unless the selected embodiment of anchoring catheter 28 includes optional perfusion ports 48, as described above. Temporary occlusion at a vessel location proximal to targeted obstruction 14 is useful to prevent distal embolization by plaque debris that may be dislodged during angioplasty and subsequently entrained in the blood flow. Proximal occlusion to prevent distal embolization typically includes the aspiration of potentially contaminated blood following dilatation, but prior to deflating balloon 46, which allows blood flow to resume. Aspiration can be performed through interior lumen 27 of anchoring catheter 28 by drawing a partial vacuum at the proximal end thereof, using for example, a syringe.

Other methods of inserting the catheter assembly 10 into the artery 12 can be used depending upon need and preference. For example, the guidewire 16 may be inserted through the proximal end of the guiding catheter 50 to its desired position. Then, the anchoring catheter 28 can be loaded on the proximal end of the guidewire 16 by inserting the proximal end of guidewire 16 into the distal end of the anchoring catheter 28, extending the wire 16 proximally through the lumen 27 of anchoring catheter 28, and then exiting from the anchoring catheter 28 through opening 32. The anchoring catheter 28 can then be advanced distally through the guiding catheter 50 and into position extending distally there from, while the guidewire 16 is manually held in position. The balloon dilatation catheter 18 is then loaded on the proximal end of the guidewire 16, is advanced through guiding catheter 50, enters anchoring catheter 28 through opening 32, and follows the guidewire 16 to its desired position in the artery.

Alternatively, the balloon catheter 18 may be loaded onto the guidewire 16 and advanced through guiding catheter 50 into the vessel to be treated. The clinician may decide to use the anchoring catheter 28, which is then loaded onto the balloon dilatation catheter 18 before advancing the anchoring catheter 28 to its desired position. Such a maneuver requires the proximal end of balloon catheter 18 to be small enough to allow anchoring catheter 28 to pass there over. Such a low profile can be achieved by temporarily removing any proximal fitting(s) mounted on balloon catheter 18, as will be recognized by one of skill in the art of balloon catheters.

Once the catheter assembly 10 is in place, the position of the guidewire 16 can be maintained if either the balloon dilatation catheter 18 or the anchoring catheter 28 needs to be withdrawn and exchanged. For example, if the operator advances the guidewire 16 down the coronary artery 12 but cannot subsequently advance the balloon dilatation catheter 18 over the guidewire 16, then the guidewire 16 can remain in place as the balloon dilatation catheter 18 is removed and another treatment catheter is loaded onto the proximal end of the guidewire 16. Similarly, if the anchoring catheter 28 is obstructing advancement of the balloon dilatation catheter 18 or malfunctions, anchoring catheter 28 can be withdrawn and/or exchanged while the intracoronary position of guidewire 16 is maintained. Thus, an operator is able to grasp the guidewire 16 while advancing or withdrawing the balloon dilatation catheter 18 or the anchoring catheter 28, thus giving the operator control of the guidewire 16 during the assembly, withdrawal, or exchange of the balloon dilatation catheter 18 and/or the anchoring catheter 28. This prevents the operator from losing the guidewire 16 position in coronary artery 12, such as withdrawing the guidewire 16 from its desired position.

Figure 4:
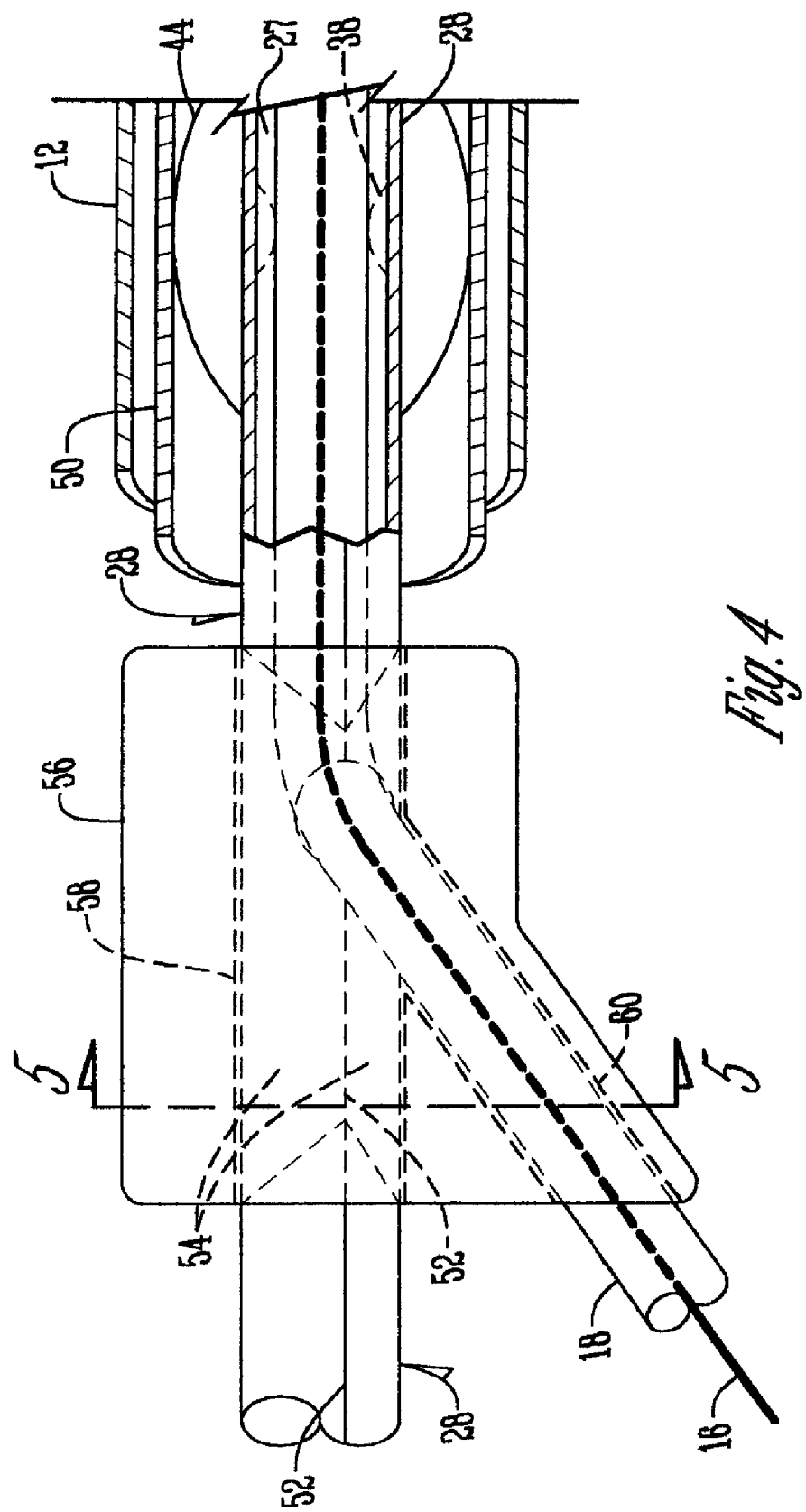
FIG. 4 is a sectional view of an alternative embodiment of the angioplasty catheter assembly wherein the opening in the tubular member of the anchoring catheter is a slit.

In an alternative embodiment, as shown in FIG. 4, the opening 32 in the outer wall 30 of the anchoring catheter 28 is comprised of an elongated longitudinal opening or slit 52 that extends from the proximal end of the anchoring catheter 28 towards the distal end of the anchoring catheter 28. Slit 52 also extends transversely from the outer wall 30 of anchoring catheter 28 to the lumen 27 thereof. The slit 52 may be considered as defining a pair of flaps 54 which normally close together at the slit 52.

Figure 5:
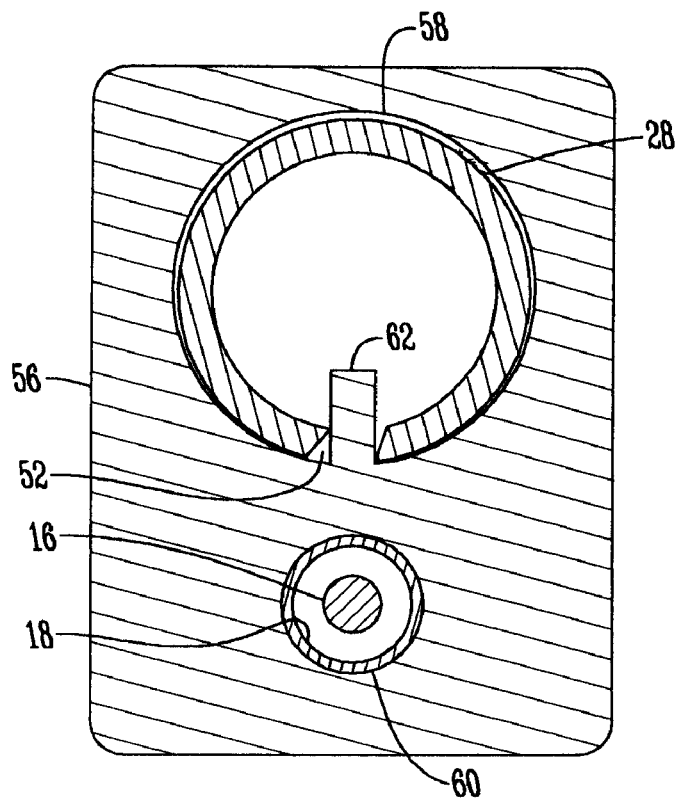
FIG. 5 is a cross-sectional view of the guide member of an enlarged scale taken on line 5-5 of FIG. 4.

Slidably mounted on the anchoring catheter 28 is a guide member 56. The guide member 56 facilitates the insertion of the balloon dilatation catheter 18, and/or the guidewire 16 transversely through the slit 52 in the anchoring catheter 28. The guide member 56 has distal and proximal ends and a first passageway 58 that extends through the length of guide member 56 and receives the anchoring catheter 28. The guide member 56 also has a second passageway 60 that extends from the proximal end of the guide member 56 and into the first passageway 58 before reaching the distal end of the guide member 56. The second passageway 60 receives the guidewire 16 and/or the balloon dilatation catheter 18. As shown in FIG. 5, a spreader member 62 is formed in the body of the guide member 56 and projects into the first passageway 58 adjacent the distal end of the first passageway 58.

Wherever the guide member 56 is slidably positioned along the anchoring catheter 28, the spreader 62 engages and extends through the slit 52 to spread flaps 54 apart, thus allowing transverse access to the lumen 27 of anchoring catheter 28 by the guidewire 16 and/or the balloon dilatation catheter 18 as they extend through the second passageway 60. Under the influence of the inherent resiliency of the flaps 54 of the outer wall 30 of the anchoring catheter 28, the flaps 54 will draw together to close the slit 52 of the anchoring catheter 28.

The guide member 56 can be moved along the length of the anchoring catheter 28 to allow the physician to adjust the insertion point created by the spreader member 62 in the slit 52. This provides the physician greater flexibility and control to assemble, withdraw, or exchange either the balloon dilatation catheter 18 or the anchoring catheter while maintaining the desired position of the guidewire 16.

Figure 6:
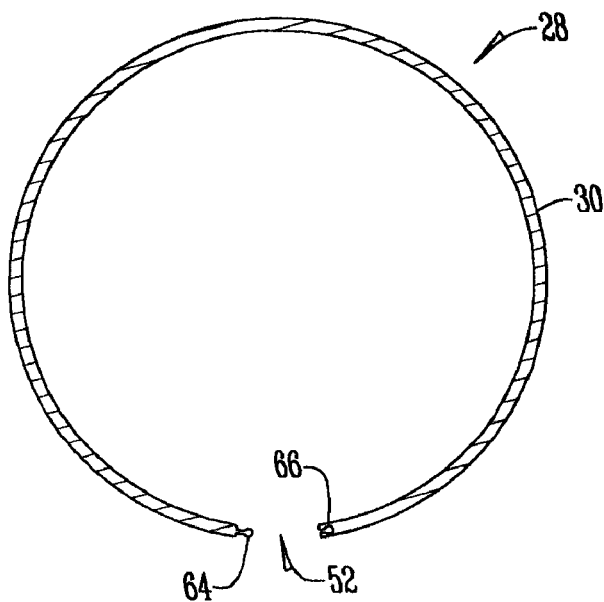
FIG. 6 is an end view of an anchoring catheter tube wall embodiment having tongue and groove members sealing the elongated longitudinal slit.

To ensure that there is not excessive leakage through the elongated longitudinal slit 52, several interlocking flap designs may be used for sealing of the flaps 54 of the elongated longitudinal slit 52. Examples of these sealing methods for adaptation to the slit 52 of the anchoring catheter 28 are shown in U.S. Pat. No. 5,171,222 incorporated by reference herein. As one example, one edge of flap 54 has a tongue member 64 that extends along the length of slit 52 and the edge of the opposite flap 54 has a groove member 66 that likewise extends along the length of slit 52 as shown in FIG. 6. The stiffness of the outer wall 30 forces flaps 54 together such that the tongue member 64 interlocks with the groove member 66 under pressure to create a seal. The flaps 54 and the tongue member 64 and groove member 66 are preferably made of a soft elastomer that is separable such that the spreader member 62 separates the flaps 54 to create an opening in the slit 52. One skilled in the art would know that this is just one example of how the elongated longitudinal slit could be sealed to help prevent leakage.

It is therefore seen that this invention will accomplish at least all of its stated objectives.

What is claimed is:

1. A method for performing angioplasty, comprising:
   inserting a guide wire through a treatment catheter to form a treatment catheter assembly;
   inserting the treatment catheter assembly through an opening in a tubular wall of an anchoring catheter to form a unit;
   inserting a guiding catheter into a patient such that the distal end of the guiding catheter is inserted into the origin of the patient's artery;
   inserting the unit through the guiding catheter;
   extending the anchoring catheter partially out of the guiding catheter and into the blood vessel;
   securing the anchoring catheter to the blood vessel;
   sliding the treatment catheter through the opening in the tubular wall of the anchoring catheter and along the guide wire until a treatment element disposed on the treatment catheter is adjacent a plaque area of the blood vessel;
   actuating the treatment element to treat the plaque area of the blood vessel.

2. The method of claim 1 further comprising deflating an external balloon and withdrawing the treatment catheter, guide wire, anchoring catheter and guiding catheter from the patient.

3. The method of claim 1 wherein the opening in the tubular wall of the anchoring catheter is a slit extending between the distal end and proximal end housing of the anchoring catheter.

4. The method of claim 3 wherein a guide member is slidably mounted on the anchoring catheter and facilitates the insertion of the treatment catheter through the slit.

5. The method of claim 3 wherein the slit has a means for releaseably sealing the slit.

6. The method of claim 1 wherein the step of securing the anchoring catheter to the blood vessel comprises inflating a first external balloon attached to the anchoring catheter.

7. The method of claim 1 further comprising the step of inflating an external balloon attached to the anchoring catheter to engage the guiding catheter and fix the anchoring catheter against movement relative to the guiding catheter.

8. The method of claim 6 further comprising the step of inflating a second external balloon attached to the anchoring catheter to engage the guiding catheter and fix the anchoring catheter against movement relative to the guiding catheter.

9. The method of claim 1 wherein an internal anchoring balloon extends inwardly within the anchoring catheter.

10. The method of claim 9 further comprising the step of inflating the internal anchoring balloon to engage the treatment catheter.

\* \* \* \* \*